(12) United States Patent
Mosimann

(10) Patent No.: US 6,319,003 B2
(45) Date of Patent: Nov. 20, 2001

(54) QUICK FIT REVOLVING CONNECTING UNIT FOR CONNECTING A DENTAL INSTRUMENT TO A POWER SUPPLY

(75) Inventor: Vincent Mosimann, La Neuveville (CH)

(73) Assignee: Bien-Air S.A., Bienne (CH)

( * ) Notice: Subject to any disclaimer, the term of this patent is extended or adjusted under 35 U.S.C. 154(b) by 0 days.

(21) Appl. No.: 09/816,419

(22) Filed: Mar. 26, 2001

(30) Foreign Application Priority Data

Apr. 14, 2000 (EP) .................................................. 00201337

(51) Int. Cl.[7] .................................................. A61C 1/08
(52) U.S. Cl. .................................................. 433/126
(58) Field of Search .................................. 433/126, 115

(56) References Cited

U.S. PATENT DOCUMENTS

| | | | |
|---|---|---|---|
| 4,403,959 | * 9/1983 | Hatakeyama | 433/126 |
| 4,534,734 | 8/1985 | Lares | 433/126 |
| 4,978,297 | * 12/1990 | Vlock | 433/88 |
| 5,057,015 | * 10/1991 | Fleer | 433/126 |
| 5,476,379 | * 12/1995 | Disel | 433/126 |
| 5,511,977 | * 4/1996 | Futch, Jr. | 433/126 |
| 5,733,117 | * 3/1998 | Coss et al. | 433/85 |
| 5,868,571 | * 2/1999 | Nakanishi | 433/126 |
| 6,033,220 | 3/2000 | Mosimann | 433/126 |

FOREIGN PATENT DOCUMENTS 98 29052   7/1998 (WO) .

\* cited by examiner

Primary Examiner—John J. Wilson
(74) Attorney, Agent, or Firm—Sughrue, Mion, Zinn, Macpeak & Seas, PLLC

(57) ABSTRACT

In order to allow a dental instrument such as an air turbine or an electric motor hand piece to be quickly connected or disconnected to a supply unit, a revolving connecting unit is provided with a fixed portion (4), provided with channels (13 to 16) for fluids and electric contact rings (26) at the front, a coupling sleeve (32) freely rotating on the fixed portion, an a stop ring inserted between said sleeve and the fixed portion and rotating freely thereon. The coupling sleeve (32) is secured to the back of the instrument by a bayonet device (38). This sleeve extends far enough forwards to prevent accidental contact between the electric contact rings (26) and an external object when the connecting unit is not connected to an instrument.

10 Claims, 3 Drawing Sheets

QUICK FIT REVOLVING CONNECTING UNIT FOR CONNECTING A DENTAL INSTRUMENT TO A POWER SUPPLY

The present invention concerns a quick fit revolving connecting unit for connecting a dental instrument to a supply unit, said connecting unit including:

a hose able to be connected to the supply unit and including electric conductors and at least one fluid conduit, a fixed portion having a rear end connected to the hose and a front end provided with a group of electric contact rings connected to said conductors, said rings being visible on a peripheral surface of the fixed portion to allow an electric connection via revolving contact with the instrument, a set of channels passing through said fixed portion to allow the or each fluid conduit of the hose to communicate with the instrument, and a rotating portion rotating freely around the fixed portion and including a coupling sleeve provided with a mechanical coupling device intended to co-operate with the instrument.

In conventional dental instruments, connecting units of this type are used to connect dental instruments, such as turbine, electric motor, light source or other handpieces, to a fixed supply and control unit including one or more fluid supply sources, an electric power supply and electric control circuits. These connecting units increasingly tend to be of a multi-purpose nature, allowing different types of dental instruments to be connected in succession to the same connecting unit.

International Patent Application WO 98/29052 discloses a revolving connecting unit called an attachment, which has the features indicated in the above preamble and further includes an additional interchangeable coupling piece, rotatably fitted onto the fixed portion. This additional coupling piece is intended to be fitted against the rear end of a dental instrument and therefore has a frontal face which specifically corresponds to the configuration of the rear face of the instrument. The additional coupling piece is held axially and in a rotatable manner on the fixed portion by means of a rotating stopping ring which is screwed thereon. The instrument itself is held axially by means of a coupling sleeve which rests on the additional coupling piece and is screwed onto the rear end of the instrument. When this sleeve is unscrewed, it can be slid backwards above the fixed portion and the hose to access the stopping ring and to actuate the latter in order to change the additional coupling piece as required, if another instrument with a different configuration has to be connected.

The presence of an additional coupling piece acting as an interface between the fixed portion of the connecting unit and the dental instrument has the drawback of increasing the total length of the apparatus carried in the dentist's hand. In these circumstances, the flexible hose connected to the rear tends to exert a torque on the apparatus which becomes higher the further the rear end of the apparatus is from the dentist's hand, and this torque can affect the accuracy of the dentist's gestures. One of the objects of the present invention is thus to create a multi-purpose revolving connecting unit which allows to reduce the length of the hand-held assembly as much as possible.

A basic idea of the invention consists in arranging the connecting unit so as to be able to omit the aforementioned additional coupling piece, the fixed portion of the connecting unit then being arranged to fit directly onto the rear end of the instrument. Thus, use is made of the fact that this fixed portion constitutes a multi-purpose element since the electric contacts and channel outlets which it has at the front allow revolving or non-revolving instruments to be connected to it, as well as instruments which use only fluids, or only power or electric signals, or both. In fact, the rear end of the instrument need only have a complementary configuration to that of the front end of the connecting unit which also allows one to revolve on the other.

However, this concept poses two particular problems. On the one hand, given that with increasing health requirements, instruments have to be sterilised between each patient, the coupling and uncoupling of the instruments to and from the connecting unit must be able to be effected simply and quickly. On the other hand, since the electric contact rings are visible on the sides of the prominent front portion of the connecting unit, it is desirable to protect them from accidental contact with foreign bodies, which could cause short-circuiting, or dirty or damage the electric contact surfaces.

These objects are achieved by a revolving connecting unit of the type indicated in the preamble, characterised in that stop means, allowing the coupling sleeve to rest axially on the fixed portion in a rotatable manner to pull the instrument backwards against the connecting unit, are inserted between said sleeve and said fixed portion, and in that the coupling sleeve extends forwards over a sufficient length to surround the group of contact rings and to prevent accidental contact between these rings and an external object when the connecting unit is not connected to an instrument.

As a result of this arrangement, the operator can connect an instrument to the connecting unit very simply and quickly, by inserting the fixed portion of the connecting unit into the back of the instrument and by rotating the coupling sleeve to effect the mechanical coupling, preferably achieved by means of a bayonet fitting. The same operations in reverse also allow quick uncoupling, which allows easy replacement of one instrument by another. The assembly also has the desired features of small length and protection of the electric contact parts, in accordance with the objects of the invention.

Other features and advantages of the invention will appear in the following description of a preferred embodiment, given by way of non limiting example with reference to the annexed drawings, in which.

Figure 1:
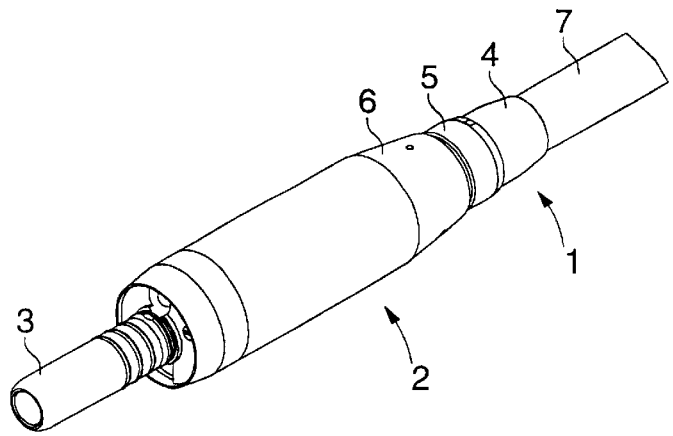
FIG. 1 shows in perspective a revolving connecting unit coupled to an electric motor intended to actuate a dental handpiece.
Figure 2:
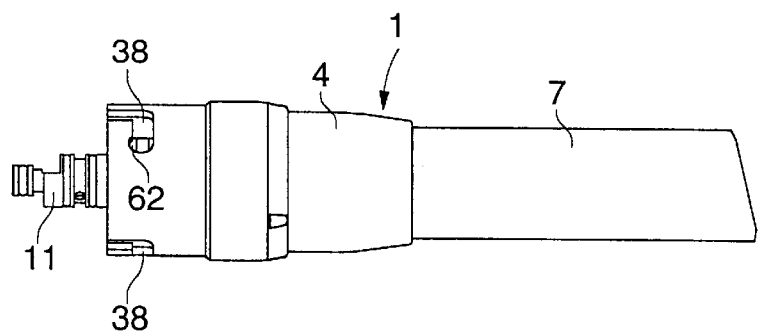
FIG. 2 is a lateral view of the revolving connecting unit.

FIG. 1 shows a revolving connecting unit 1 connected to the back of an electric motor 2 which constitutes a dental instrument with a handpiece which is not shown, fitted onto the front end 3 of motor 2. Connecting unit 1 includes a fixed portion 4, rotatably fitted into the rear end of motor 2, and a rotating portion 5 provided with a bayonet coupling device co-operating with rear end 6 of electric motor 2.

Connecting unit 1 also includes a flexible hose 7 the front end of which is connected to fixed portion 4, while the other end (not shown) is connected to a supply and control unit of the type described above. This known element will not be described in detail here.

Revolving connecting unit 1 is described in more detail hereinafter with reference to FIGS. 2 to 6. As can be seen in particular in FIG. 5, fixed portion 4 of the connecting unit includes a rear body 10 and a front body 11, fitted to each other and secured by a threaded ring 12. Four channels for fluids 13 to 16 pass through these two bodies, namely a cooling fluid channel 13 for the work area, a compressed air channel 14 capable of driving a pneumatic turbine motor or cooling an electric motor, a compressed air channel 15 for air to be projected onto the work area, and a return air channel 16. At the back of body 10, these four channels open out into four joining pieces 17, 18 communicating with conduits 19, 20 arranged in a known manner in flexible hose 7. The latter further contains four electric conductors 21, only one of which is shown. Hose 7 is secured to rear body 10 using two conical sleeves 22 and 23 and a threaded ring 24 which also belong to the fixed portion of the connecting unit.

A group of four electric contact rings 26 is mounted on a cylindrical portion of front body 11 by means of an insulating support 27, the ring and support assembly having a cylindrical peripheral surface 28 intended to be fitted into a corresponding housing of the instrument. Each ring 26 is electrically connected, in a way which is not shown, to one of conductors 21 of hose 7 to be connected, for example, to a power supply including three phases and a neutral pole.

Figure 6:
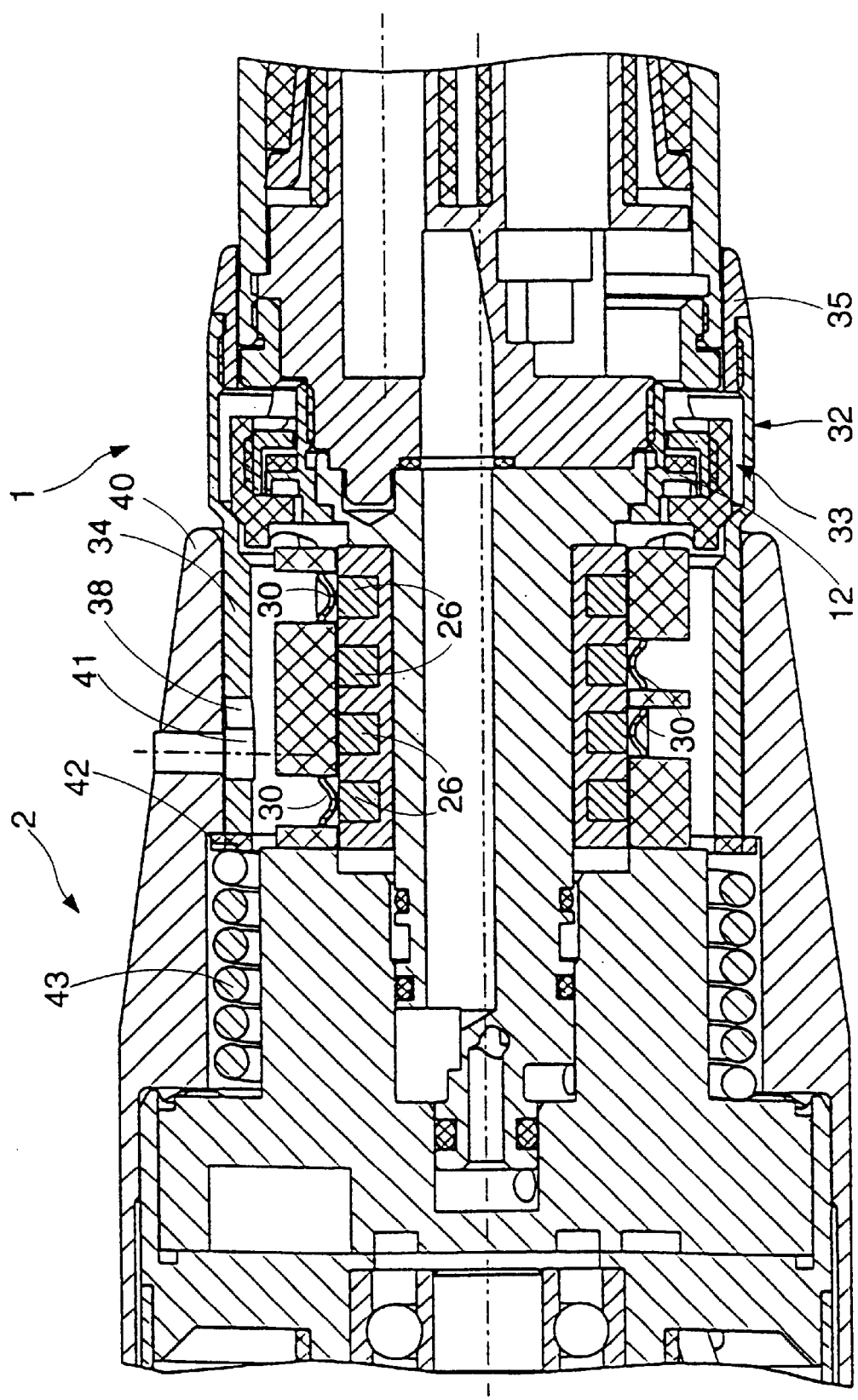
FIG. 6 is a similar view to FIG. 5, further showing the rear end of the electric motor connected to the revolving connecting unit.

As FIG. 6 shows, when revolving connecting unit 1 is connected to the rear end of electric motor 2 or another instrument having a similar rear configuration, the external surface of each contact ring 26 will be in sliding contact with a corresponding wiper 30 formed by a resilient strip connected to the inner circuits of the motor and thus allowing the handpiece to be powered via the motor, if required.

Figure 5:
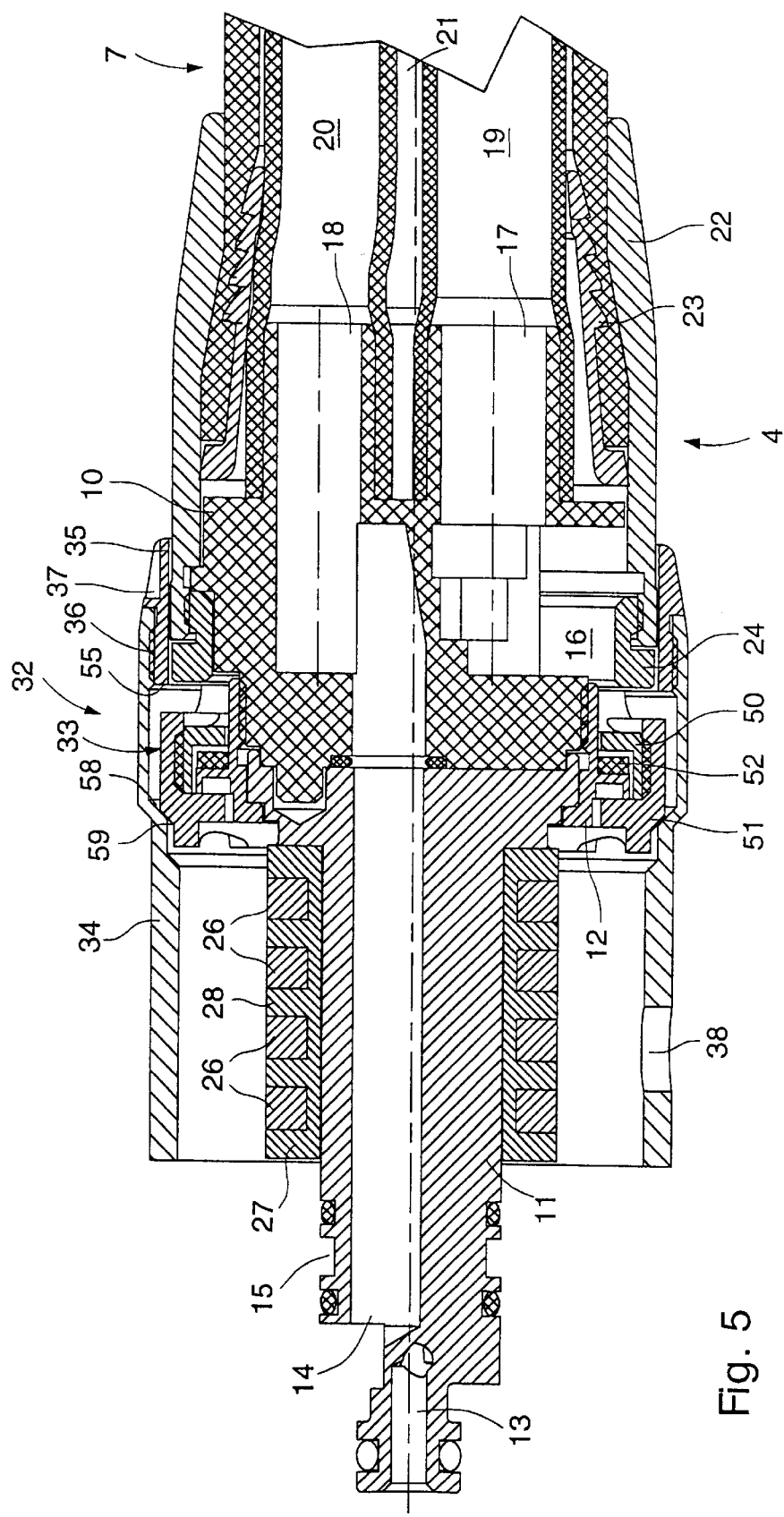
FIG. 5 is a general longitudinal cross-section of the revolving connecting unit.

The rotating portion of the revolving connecting unit includes, as is seen better in FIG. 5, a coupling sleeve 32 and an intermediate stopping ring 33 arranged between sleeve 32 and threaded ring 12 which belongs to the fixed portion of the connecting unit.

Coupling sleeve 32 includes a substantially cylindrical bush 34 and an annular nut 35 secured to the back of bush 34 by a threading 36. Hollows 37 are arranged on the external surface of nut 35 to act as a gripping member. Bush 34 extends forwards over a sufficient length to surround the group of contact rings 26, thus preventing them from being able to touch any external object, for example the operator's fingers while he is changing instruments on the connecting unit. Bush 34 further assures the mechanical coupling between the connecting unit and the instrument, as a result of a bayonet device including at least two notches 38 (three notches in the present case) in the shape of a J, which can be seen more clearly in FIG. 2. FIG. 6 shows that bush 34 of the coupling sleeve fits into a rear joining piece 40 of electric motor 2, provided with snugs 41 which engage in notches 38 of bush 34 to secure the motor axially to the connecting unit. Within joining piece 40, a support washer 42 pushed backwards by the spring 43 assures the locking of snugs 41 at the bottom of J-shaped notches 38.

It will be noted that nut 35, and with it the whole of coupling sleeve 32, can not only rotate, but also slide axially along the outer cylindrical surface of element 22 of the fixed portion of connecting unit 1.

Figure 3:
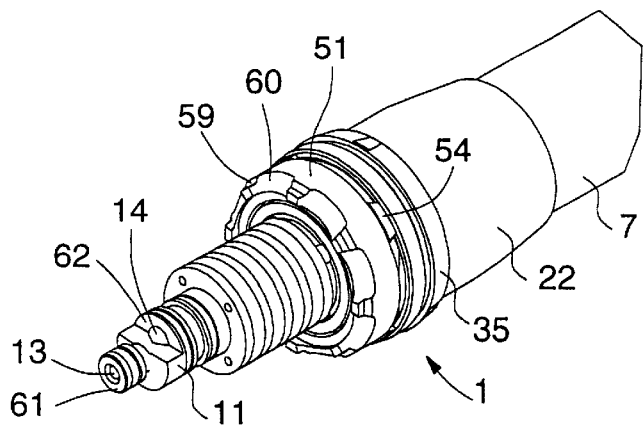
FIG. 3 is a perspective view of the revolving connecting unit, from which certain elements have been removed to show internal details.

The intermediate ring 33 acting as an axial stop for coupling sleeve 32 has a U-shaped cross-section and overlaps fixed ring 12 with axial play. It is formed of two threaded rings 50 and 51 screwed into each other. Fixed ring 12 carries a ring 52 made of an antifriction material, for example PTFE, against which inner ring 50 can rest axially by sliding. Antifriction ring 52 could be replaced by a ball thrust bearing or another type of stop unit. In FIG. 3 connecting unit 1 is shown without bush 34, which is actually removable, and in FIG. 4 ring 51 has also been omitted, in order to see the stop means of the coupling sleeve more clearly. Rear ring 50 includes snugs 54, which are four in number here, which project outwards and backwards and act as a stop for front end 55 of nut 35. Air conduit 16 indicated in FIG. 5 passes between snugs 54 to bypass ring 50.

Figure 4:
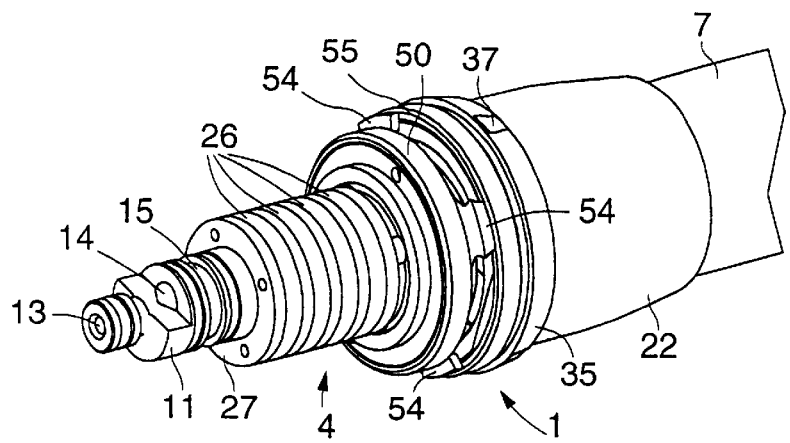
FIG. 4 is a similar view to FIG. 3, from which a ring has also been removed.

It will also be noted that bush 34 has an inner shoulder 58 intended to abut against a frontal surface 59 of back ring 51, to prevent coupling sleeve 32 being able to come too far backwards when it is not coupled to an instrument, in the situation shown in FIG. 4. The axial distance between shoulder 58 and end 55 of the nut is large enough to arrange an axial play of sleeve 32 on intermediate stop ring 33. When sleeve 32 is coupled to an instrument, it is drawn forwards and its shoulder 58 moves away from ring 51. The air flowing in channel 16 can pass freely between them under any circumstances as a result of nicks 60 (FIG. 3) arranged in surface 59 of ring 51.

Electric motor 2 or any other instrument fitted onto the revolving connecting unit is generally pushed forwards by the pressured fluids contained in one or more of channels 13 to 16. It is held axially by a force passing through bayonet device 38, 41, sleeve 32, frontal surface 55 of nut 35, intermediate ring 33 and antifriction ring 52 to be transmitted to the fixed portion of the connecting unit. In particular, the pressure of the water in channel 13 acts on a frontal face 61 (FIG. 3) of the fixed portion of the connecting unit, the pressure of the compressed air in channel 14 acts on another frontal face 62 of this fixed portion, and the pressure of the return air in channel 16 also acts on the fixed portion in the region of intermediate ring 33. Each of these pressures pushes the fixed portion backwards. The effect of this pushing is to block snugs 41 in the ends bent forwards 62 of J-shaped notches 38 (FIG. 2), which increases the force necessary to open the bayonet coupling device and consequently increases the coupling security. When the fluid supply is stopped, these pressures disappear thus facilitating uncoupling.

The construction described hereinbefore allows the operator easily to couple and uncouple any instrument such as motor 2 to or from connecting unit 1, simply by gripping the instrument with one hand and rotating coupling sleeve 32 with the other hand to operate the bayonet device. Thus, the replacement of an instrument with another is extremely quick. As a result of the multiple possibilities of different supplies of electricity and fluids which are offered by the connecting unit according to the invention, it can be directly connected to a great variety of dental instruments, using one or more of the supply possibilities.

What is claimed is:

1. A quick fit revolving connecting unit for connecting a dental instrument to a supply unit, said connecting unit including:
    a hose able to be connected to said supply unit and including electric conductors and at least one fluid conduit,
    a fixed portion having a rear end connected to said hose and a front end provided with a group of electric contact rings connected to said conductors, said contact rings being visible on a peripheral surface of said fixed portion to allow an electric connection via revolving contact with the instrument, a set of channels passing through said fixed portion to allow the or each fluid conduit of the hose to communicate with the instrument, and a rotating portion rotating freely around said fixed portion and including a coupling sleeve provided with a mechanical coupling device for co-operating with the instrument, wherein stop means, allowing said coupling sleeve to rest axially on said fixed portion in a rotatable manner to pull the instrument backwards against the connecting unit, are inserted between said sleeve and said fixed portion, and wherein said coupling sleeve extends forwards over a sufficient length to surround said group of contact rings and to prevent accidental contact between said contact rings and an external object when the connecting unit is not connected to an instrument.

2. A connecting unit according to claim 1, wherein said mechanical coupling device is a bayonet device.

3. A connecting unit according to claim 2, wherein said coupling sleeve has an axial play with respect to said stop means, wherein said bayonet device includes J-shaped notches, each intended to accommodate a snug of the instrument, and wherein said set of channels includes at least a channel opening out into a frontal face at the front of said fixed portion and arranged to convey a fluid under pressure, so that the pressure of said fluid tends to block said snugs in said notches when an instrument is connected to the connecting unit.

4. A connecting unit according to claim 1, wherein said coupling sleeve has an axial play with respect to said stop means.

5. A connecting unit according to claim 1, wherein said coupling sleeve includes a removable bush, surrounding said contact rings and provided with said mechanical coupling device at its front end, and an annular nut engaged by screwing into a rear end of said bush and mounted so as to rotate and slide on said fixed portion.

6. A connecting unit according to claim 5, wherein said removable bush has an inner shoulder arranged to be able to abut against a frontal surface of said stopping means and wherein said annular nut is arranged to abut against a rear surface of said stopping means.

7. A connecting unit according to claim 6, wherein said stopping means include an intermediate ring arranged to abut axially and in a rotatable manner against said fixed portion and against said coupling sleeve, wherein said rear surface of the stopping means is formed by projecting portions of said intermediate ring, and wherein one of said channels, intended to convey return air from the instrument, passes between said intermediate ring and said coupling ring and between said projecting portions to reach said fixed portion of the connecting unit.

8. A connecting unit according to claim 7, wherein said channel intended to convey return air passes through nicks arranged in said frontal surface of said stopping means.

9. A connecting unit according to claim 1, wherein said stopping means include an intermediate ring arranged to abut axially and in a rotatable manner against said fixed portion and against said coupling sleeve.

10. A connecting unit according to claim 9, wherein said intermediate ring is mounted with an axial play on said fixed portion and abuts it axially via a ring made of antifriction material.

* * * * *